United States Patent [19]

Byford et al.

[11] Patent Number: 5,909,671
[45] Date of Patent: Jun. 1, 1999

[54] SYSTEM AND METHOD FOR CONTROLLING DATA ACCESS IN A COMPUTER NETWORK

[75] Inventors: Derrick John Byford, Cafford; Graham Boydell, Southrop, both of United Kingdom

[73] Assignee: International Business Machines Corporation, Armonk, N.Y.

[21] Appl. No.: 08/794,940

[22] Filed: Feb. 4, 1997

[30] Foreign Application Priority Data

Aug. 3, 1996 [GB] United Kingdom .................... 9616396

[51] Int. Cl.⁶ ................................................. G06F 15/163
[52] U.S. Cl. .......................... 705/26; 705/27; 395/200.47; 395/200.49; 395/200.61
[58] Field of Search .................................. 705/26, 18, 27; 395/200.47, 200.49, 200.61, 200.33

[56] References Cited

U.S. PATENT DOCUMENTS

| 5,003,584 | 3/1991 | Benyacar et al. . |
| 5,148,474 | 9/1992 | Haralambopoulous et al. . |
| 5,220,501 | 6/1993 | Lawlor et al. . |
| 5,737,414 | 4/1998 | Walker et al. ............................... 380/4 |

FOREIGN PATENT DOCUMENTS

| 0 643 541 | 3/1995 | European Pat. Off. . |
| 2 280 820 | 2/1995 | United Kingdom . |
| 9524688 | 9/1995 | WIPO .............................. G06F 19/00 |
| 9608783 | 3/1996 | WIPO .............................. G06F 17/60 |

OTHER PUBLICATIONS

Proceedings of the Symposium on Network and Distributed System Security, Jan. 1, 1995, "Electronic Cash on the Internet" by Stefan Brands, pp. 64–84.

*Primary Examiner*—Thomas R. Peeso
*Attorney, Agent, or Firm*—Edward H. Duffield

[57] ABSTRACT

A system for controlling data access in a computer network comprises first means for establishing a first communication link between a client computer and a server computer. The client sends a request to the server for supply of a data item from the server to the client. The server selects the requested data item from a store of data items in response to the request from the client. The server associates each data item in the store with a service telephone number. The server also identifies a subscriber telephone number associated with the request. A second communication link is then established between the server and a telephone utility. The server instructs the telephone utility to register a telephone call from the subscriber telephone number to the service telephone number associated with the requested data item. The requested data item is supplied from the server to the client on receipt by the server of confirmation from the telephone utility that the telephone call is registered.

18 Claims, 4 Drawing Sheets

---

PERSONAL FORECASTING SERVICE

Welcome to the XYZ personal forecasting service. To receive your forecast for the region of your choice for any time period up to two weeks ahead complete the information below and submit.

| REGION | DAY | | TIME PERIOD |
|---|---|---|---|
| | W/B 12/6 | W/B 19/6 | |
| () SW | () MON | () MON | () MIDNIGHT - 6.00 AM |
| () SE | () TUE | () TUE | () 6.00 AM - NOON |
| () MIDLANDS | () WED | () WED | () NOON - 6.00 PM |
| () NE | () THU | () THU | () 6.00 PM - MIDNIGHT |
| () NW | () FRI | () FRI | |
| () SCOTLAND | () SAT | () SAT | {SUBMIT} |
| | () SUN | () SUN | |

1 XYZ HOME PAGE 1   1 ABC HOME PAGE 1

PERSONAL FORECASTING SERVICE

Welcome to the XYZ personal forecasting service. To receive your forecast for the region of your choice for any time period up to two weeks ahead complete the information below and submit.

| REGION | DAY | | TIME PERIOD |
|---|---|---|---|
| | W/B 12/6 | W/B 19/6 | |
| () SW | () MON | () MON | () MIDNIGHT - 6.00 AM |
| () SE | () TUE | () TUE | () 6.00 AM - NOON |
| () MIDLANDS | () WED | () WED | () NOON - 6.00 PM |
| () NE | () THU | () THU | () 6.00 PM - MIDNIGHT |
| () NW | () FRI | () FRI | |
| () SCOTLAND | () SAT | () SAT | {SUBMIT} |
| | () SUN | () SUN | |

1 XYZ HOME PAGE 1    1 ABC HOME PAGE 1

FIG. 5

SYSTEM AND METHOD FOR CONTROLLING DATA ACCESS IN A COMPUTER NETWORK

BACKGROUND OF THE INVENTION

TECHNICAL FIELD

The present invention relates to a system and method for controlling data access in a computer network.

In recent years, there has been explosive growth in the Internet, and in particular of the WorldWide Web (WWW), which is one of the facilities provided via the Internet. The WWW comprises many pages or files of information, distributed across many different servers. Each page is identified by a Universal Resource Locator (URL). Each URL denotes both a server machine, and a particular file or page on that machine. There may be many pages or URLs resident on a single server.

To utilise the WWW, a user runs a computer program called a Web browser on a client computer system such as a personal computer. Examples of widely available Web browsers include the "WebExplorer" Web browser provided by International Business Machines Corporation in the OS/2 Operating System software, or the "Navigator" Web browser available from Netscape Communications Corporation. The user interacts with the Web browser to select a particular URL. The interaction causes the browser to send a request for the page or file identified in selected URL to the server identified in the selected URL. Typically, the server responds to the request by retrieving the requested page, and transmitting the data for that page back to the requesting client. The client-server interaction is usually performed in accordance with a protocol called the hypertext transfer protocol ("http"). The page received by the client is then displayed to the user on a display screen of the client. The client may also cause the server to launch an application, for example to search for WWW pages relating to particular topics.

WWW pages are typically formatted in accordance with a computer programming language known as hypertext mark-up language ("html"). Thus a typically WWW page includes text together with embedded formatting commands, referred to as tags, that can be employed to control for example font style, font size, lay-out etc. The Web browser parses the HTML script in order to display the text in accordance with the specified format. In addition, an html page also contain a reference, in terms of another URL, to a portion of multimedia data such as an image, video segment, or audio file. The Web Browser responds to such a reference by retrieving and displaying or playing the multimedia data. Alternatively, the multimedia data may reside on its own WWW page, without surrounding html text.

Most WWW pages also contain one or more references to other WWW pages, which need not reside on the same server as the original page. Such references may be activated by the user selecting particular locations on the screen, typically by clicking a mouse control button. These references or locations are known as hyperlinks, and are typically flagged by the Web browser in a particular manner. For example, any text associated with a hyperlink may be displayed in a different colour. If a user selects the hyperlinked text, then the referenced page is retrieved and replaces the currently displayed page.

Further information about html and the WWW can be found in "World Wide Web and HTML" by Douglas McArthur, p18–26 in Dr Dobbs Journal, December 1994, and in "The HTML SourceBook" by Ian Graham, John Wiley, New York, 1995.

Many organisations, particularly although not exclusively those in the entertainment industry, are now seeking to generate revenue from the Internet by granting users access to WWW pages and files, particularly those containing multimedia data, subject to an access charge to the user. Such electronic commerce has been inhibited because of difficulty in providing a secure method of charging and billing for transactions over the Internet. Conventional solutions to this problem have tended to involve credit card payments and the like. Such access control methods are however uneconomical in terms of data processing to be applicable to low cost transactions over the Internet.

SUMMARY OF THE INVENTION

In accordance with the present invention, there is now provided a system for controlling data access in a computer network, the system comprising: first means for establishing a first communication link between a client computer and a server computer; means in the client for sending a request from the client to the server for supply of a data item from the server to the client; means in the server for selecting the requested data item from a store of data items in response to the request from the client; means in the server for associating each data item in the store with a service telephone number; means in the server for identifying a subscriber telephone number associated with the request; second means for establishing a second communication link between the server and a telephone utility; means in the server for instructing the telephone utility to register a telephone call from the subscriber telephone number to the service telephone number associated with the requested data item; and, means for supplying the requested data item from the server to the client on receipt by the server of confirmation from the telephone utility that the telephone call is registered.

By allowing access to networked services such as services available over the Internet subject to registration of "virtual" telephone calls, the present invention solves the problem of effecting low cost transactions in association with the services provided. The "virtual telephone call", and hence the bill for providing the service, simply appears as an item on the bill associated with the subscriber telephone number.

Preferably although not necessarily, the first establishing means comprises a web browser for establishing the first communication link via the Internet.

The store may comprise a memory in the server system.

In preferred embodiments of the present invention, the associating means comprises a look-up table stored in a memory of the server system.

In particularly preferred embodiments of the present invention, the client comprises means for identifying the subscriber telephone number to the server.

The identifying means may comprise a user input field for receiving a personal identification number from a user of the client.

The service telephone number preferably although not necessarily comprises a premium rate telephone number.

The second establishing means may generate the communication link between the server and the telephone utility via the Internet.

In especially preferred embodiments of the present invention, the data item comprises a weather forecast. In such embodiments of the present invention, the client preferably comprises means for specifying to the server the geographical location, day, and time desired for the weather forecast.

Viewing the present invention from another aspect, there is now provided a method for controlling data access in a computer network, the method comprising: establishing a first communication link between a client computer and a server computer; sending a request from the client to the server for supply of a data item from the server to the client; selecting the requested data item from a store of data items in response to the request from the client; associating each data item in the store with a service telephone number; identifying a subscriber telephone number associated with the request; establishing a second communication link between the server and a telephone utility; instructing the telephone utility to register a telephone call from the subscriber telephone number to the service telephone number associated with the requested data item; and, supplying the requested data item from the server to the client on receipt by the server of confirmation from the telephone utility that the telephone call is registered.

The present invention also extends to a personal weather forecasting system comprising: means for establishing a communication link between a client computer and a server computer; means in a client computer for sending a request from the client to the server for supply of a weather forecast from the server to the client; means in the server for selecting the requested weather forecast from a store of weather forecasts in response to the request from the client; and, means for supplying the requested weather forecast from the server to the client.

Viewing the present invention from yet another aspect, there is provided a server computer system for controlling data access in a computer network, the system comprising: first means for establishing a first communication link to a client computer; means for receiving a request from the client for supply of a data item from the server to the client; means for selecting the requested data item from a store of data items in response to the request from the client; means for associating each data item in the store with a service telephone number; means for identifying a subscriber telephone number associated with the request; second means for establishing a second communication link to a telephone utility; means for instructing the telephone utility to register a telephone call from the subscriber telephone number to the service telephone number associated with the requested data item; and, means for supplying the requested data item to the client on receipt of confirmation from the telephone utility that the telephone call is registered.

BRIEF DESCRIPTION OF THE DRAWINGS

Preferred embodiments of the present invention will now be described by way of example only with reference to the accompanying drawings, in which.

DETAILED DESCRIPTION OF THE PREFERRED EMBODIMENTS

Figure 1:
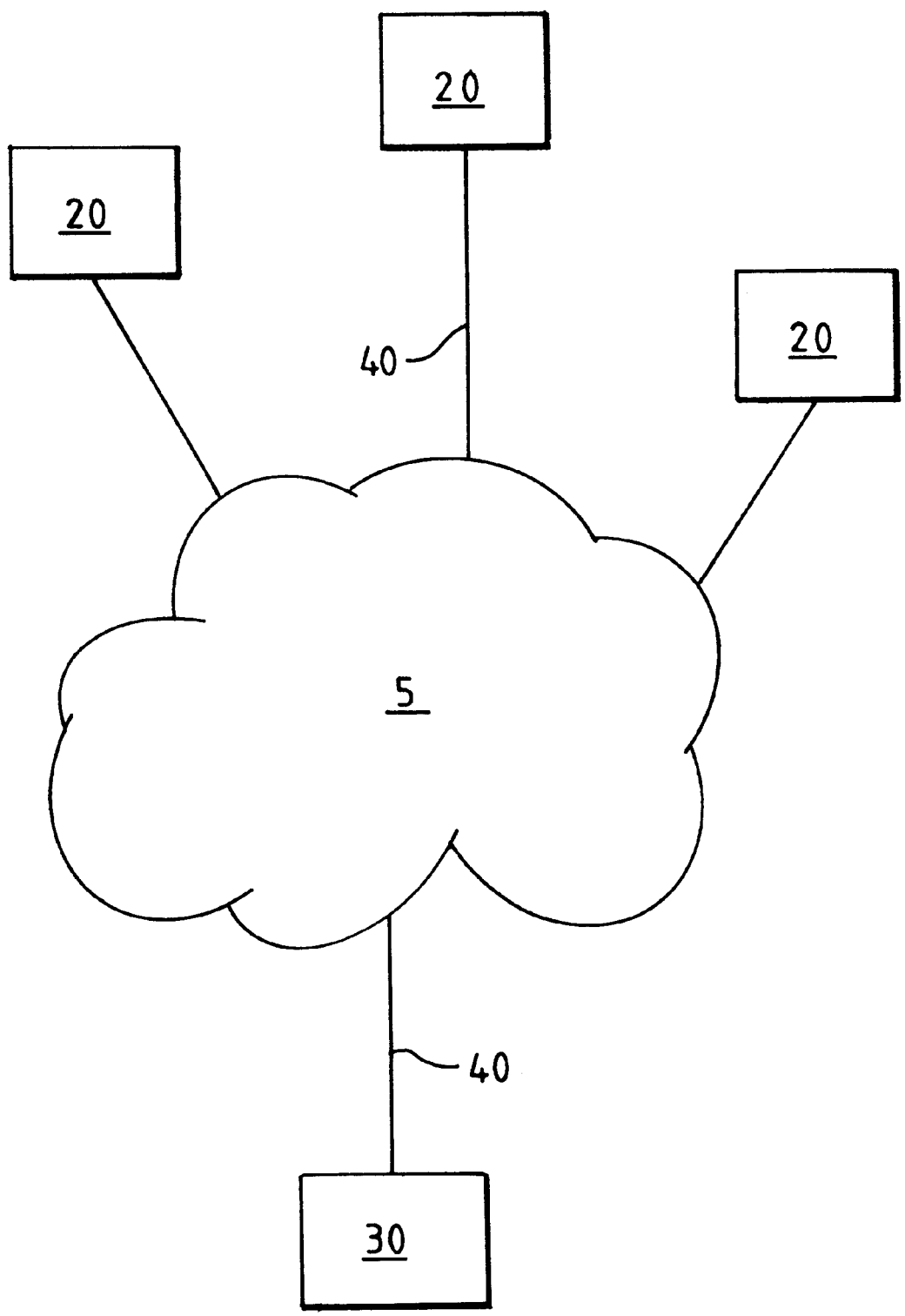
FIG. 1 is a block diagram of a computer network involving the internet.

Referring first to FIG. 1, an example of a computer network of the present invention comprises a client computer system 30 or internet terminal connectable to a plurality of different server computer systems over the Internet 5. As mentioned earlier, to establish an Internet connection 40 between one of the servers 20 and the client 30, a user runs a Web browser on the client 30. The user interacts with the Web browser to select a particular URL. The interaction causes the browser to send a request for the page or file identified in selected URL to the server 20 identified in the selected URL. Typically, the server 20 responds to the request by retrieving the requested WWW page, and transmitting the data for that page back to the requesting client 30 via the connection 40. The client-server interaction is usually performed in accordance with a protocol called the hypertext transfer protocol ("http").

Figure 2:
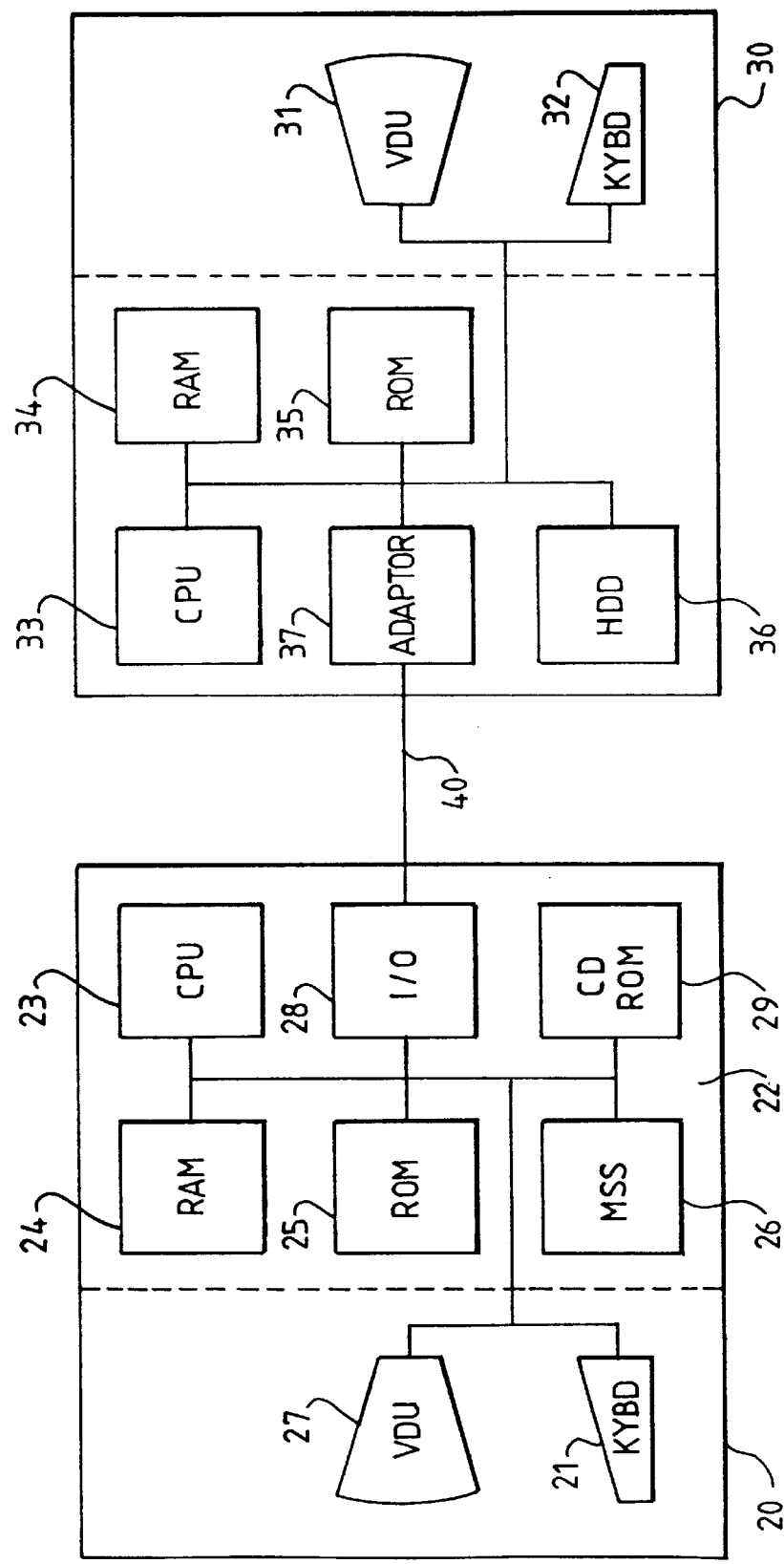
FIG. 2 is a block diagram of a client computer connected to a server computer via the internet.

Referring now to FIG. 2, a typical client 30 comprises a personal computer having a keyboard 32 and a display 32 operating under the control of control logic in the form of a main CPU 33 which is connected by a system bus to system memory (RAM) 34, non-volatile memory (ROM) 35, in which is stored system BIOS, and also to one or more storage devices such as hard disk file (HDD) 36. The web browser is normally stored in the HDD 36. However, the web browser is copied from the HDD 36 into RAM 34 when executed. The page received by the client 30 is displayed to the user on the display screen 32.

Remaining with FIG. 2, a typical server computer system 20 includes a keyboard 21 attached to a system unit 22 including a main CPU 23, system RAM 24, system ROM 25, and mass storage capability 26, typically in the form of multiple magnetic disk drives constituted in a RAID (redundant array of independent disks) arrangement. The or each WWW page provided by the server is stored in the mass storage capability 26. The server system 20 also includes a display 27 enabling direct interaction between the system 20 and an administrator. The server system 20 may also include other storage devices such as diskette drives and CD ROM drives. In some embodiments of the present invention, the display 27 and keyboard 21 of the server 20 may be coupled to the server system unit 22 via an intermediate personal computer.

Figure 3:
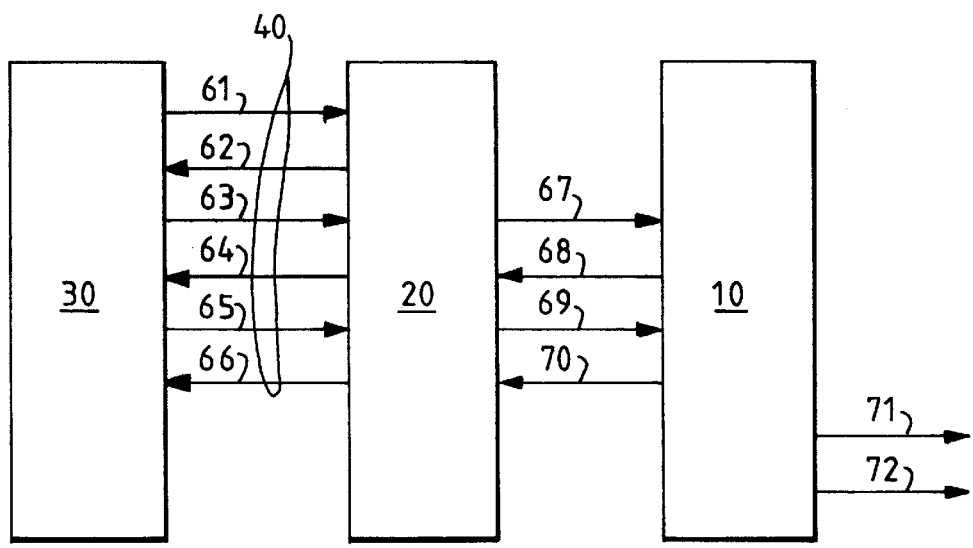
FIG. 3 is a block diagram of an example of system of the present invention.

Referring now to FIG. 3, in a preferred embodiment of the present invention, user access to WWW pages over the Internet is controlled via a transaction system comprising the client 30, the server 20, and a telephone utility 10 to which the user of the client subscribes. Each WWW page stored in the server 20 may be free access or controlled access. The free access WWW pages can be accessed free of charge by users. The controlled access WWW pages are accessible subject to a charge imposed by the page owner. Each controlled access page is accessed via a free access page. It will be appreciated that the owner of each page stored on the server 20 need not be the owner of the server 20. In some embodiments of the present invention, the WWW pages stored on the server 20 may each belong to a different owner. The server 20 comprises a look-up table (not shown) stored in the mass storage capability 26. The look-up table maps each controlled access WWW page to a premium rate telephone number.

Figure 4:
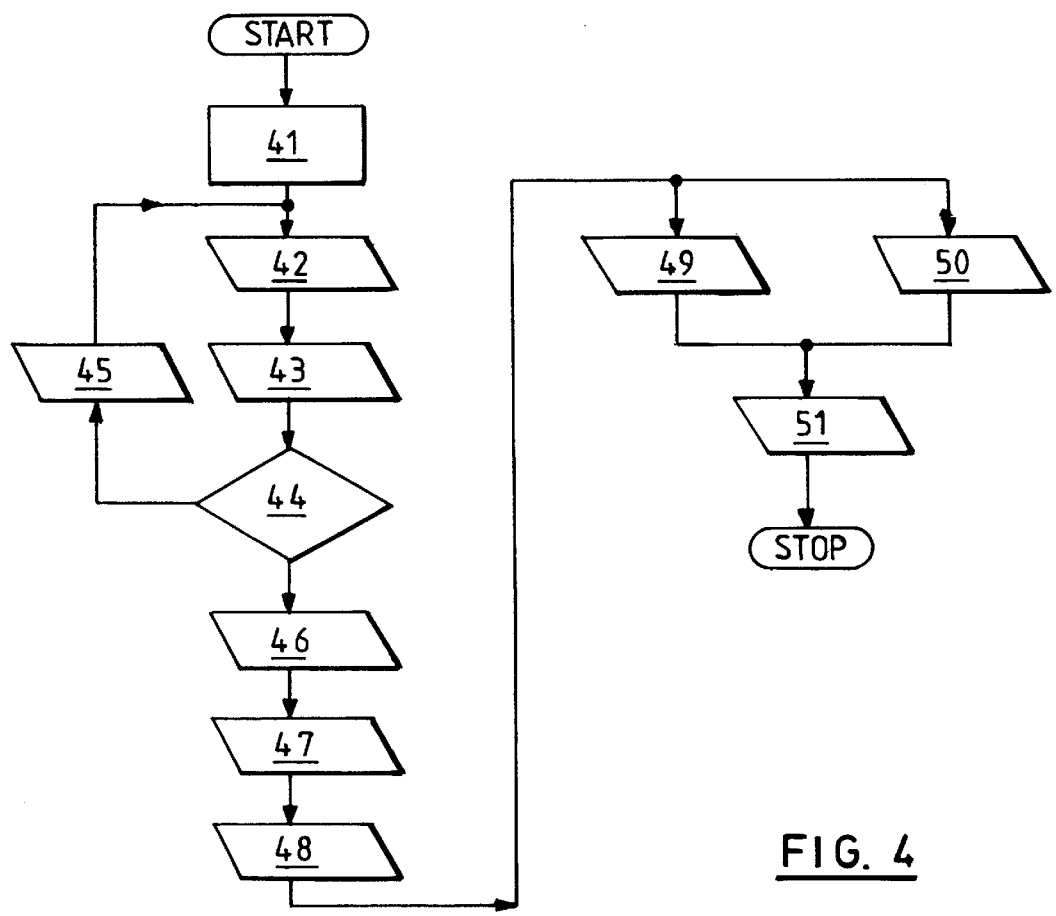
FIG. 4 is a block diagram of an example of a system of the present invention in the form of a flow chart; and, FIG. 5 is a screen generated by a client computer in an example of a system of the present invention.

Referring now to FIGS. 3 and 4 in combination, the user establishes the internet connection 40 between the client 30 and the server 20 via the web browser as indicated by transaction 61 in FIG. 3 and block 41 in FIG. 4. The server 20 responds to the connection establishing URL received from the client 30 by returning a corresponding free access WWW page to the client 30 as indicated by transaction 62 in FIG. 3 and block 42 in FIG. 4. In turn, the client 30 displays the received free access WWW page to the user.

The free access Web page may contain one or more user-selectable hypertext links to controlled access WWW pages. If the user wishes to access a controlled access Web page, he/she is requested to enter a Personal Identification Number (PIN) corresponding to his/her personal telephone number or another telephone number at his/her disposal. In particularly preferred embodiments of the present invention, the PIN is a telephone charge card number. Entry of the PIN is signified in FIG. 3 by transaction 63 and by block 43 in FIG. 4. The server 20 passes the PIN received from the client 20 to the telephone utility 10 as indicated by transaction 67 in FIG. 3. The telephone utility 10 checks the PIN received from the server 20 and indicates to the server 20 whether or not the PIN is bona-fide as indicated by transaction 68 in FIG. 3 and block 44 in FIG. 4. If the PIN is bona-fide, the server 20 indicates to the client that access is granted as indicated by transaction 64 in FIG. 3 and block 46 in FIG. 4. If the PIN is not bona-fide, the server indicates to the client that access is denied as indicated by block 45 in FIG. 4 and the user is returned to the free access WWW page at block 42 in FIG. 3. With access granted, the user selects the desired controlled access WWW page as indicated by block 47 in FIG. 4. In response to the selection, the client 30 identifies the selected WWW page to the server 20 as indicated by transaction 65 in FIG. 3. On receipt of the identification, as indicated by transaction 69 in FIG. 3 and by block 48 in FIG. 4, the server 20 instructs the telephone utility 10 to record a telephone call from the telephone number associated with the PIN to the premium rate telephone number associated with the selected WWW page by the look-up table in the server 20. The telephone utility 10 then indicates to the server 20 that a "virtual" telephone connection has been made between the telephone number associated with the PIN and the premium rate telephone number associated with the selected WWW page as indicated by transaction 70 in FIG. 3. In response to confirmation that the telephone connection is completed, the server 20 supplies the controlled access WWW page to the client 30 for display to the user as indicated by transaction 66 in FIG. 3 and block 48 in FIG. 4. The telephone utility bills the account corresponding to the telephone number associated with the PIN for the virtual telephone call to the premium telephone as indicated by transaction 71 in FIG. 3 and block 49 in FIG. 4. The charge for accessing the controlled access WWW page thus appears on the statement issued to the account holder for the telephone number associated with the PIN. The provider of the telephone utility 10 reimburses the owner of the controlled access WWW page when the bill is settled by the account holder as indicated by transaction 72 in FIG. 3 and block 51 in FIG. 4.

In some embodiments of the present invention, connection to the controlled access WWW page may invoke a single, fixed premium rate charge. In other embodiments of the present invention, connection to the controlled access WWW page may be charged on a time-dependent basis (eg: a per minute basis with peak and off-peak rates) via the premium rate call.

Referring now to FIG. 5, in an especially preferred embodiment of the present invention, the server 20 is configured to provide a personal weather forecasting system to the user via the Internet connection 40. The personal weather forecasting system includes a free access input page 80 stored in the mass storage capability of the server 30. The server 20 has access to a database of geographically and temporally arranged weather forecasts. In some embodiments of the present invention, the database may be stored integrally to the server 30 in the mass-storage capability. In other embodiments of the present invention, the database may be stored externally to the server 30. In operation, the input page 80 is displayed to the user via the display screen of the client 30. The input page 80 comprises a geographical input field 81, a time of day input field 82, and a day input field 83. In operation, the user enters: the geographical region of interest in the geographical input field 81; the time of day for which a weather forecast of interest in the time of day input field 82; and, the day of interest in the day input field 83. The server 20 responds to the user input to the input fields 81, 82 and 83, by requesting a PIN from the user. On receipt of the PIN, the server checks with the telephone utility 10 that the PIN is bona fide in the manner hereinbefore described with reference to FIGS. 3 and 4. If the telephone utility 10 informs the server 30 that PIN is bona fide, the server 20 obtains from the database the weather forecast data requested by user based on the entries to the input fields 81, and 82, and 83 supplied by the client. The weather forecast data is then sent by the server 20 to the client 30 for display to the user. Meanwhile, the server 20 retrieves the premium rate telephone number corresponding to the weather forecasting system from the look-up table. The server 30 then instructs the telephone utility 10 to place a virtual telephone call from the subscriber telephone number associated with the PIN supplied by the user to the premium rate telephone number retrieved from the look-up table. As hereinbefore described with reference to FIGS. 3 and 4, the user is thus billed for using the weather forecasting service via the account corresponding to the subscriber telephone number associated with the PIN.

In the embodiments of the present invention hereinbefore described, the subscriber telephone number to which charges for supply to controlled access WWW pages are addressed is identified to the server 20 by a PIN entered by the user, such as a PIN corresponding to a subscriber telephone charge-card. In other embodiments of the present invention, the subscriber telephone number may be identified to the server 20 in different ways. For example, in some embodiments of the present invention, the subscriber telephone number employed for the virtual telephone call may be the telephone number associated with a modem link providing the Internet connection 40 between the client 30 and the server 20.

Furthermore, in the preferred embodiments of the present invention hereinbefore described, each controlled access WWW page was associated with a premium rate telephone number. It will be appreciated however that, in other embodiments of the present invention, each controlled access WWW page may associated with other types of telephone numbers such as conventional rate telephone numbers for example.

Still furthermore, in the embodiments of the present invention hereinbefore described, the client computer system 30 comprises a personal computer. It will however now be appreciated that, in other embodiments of the present invention, the client computer system 30 may comprise a network computer, set-top box or other form of Internet access device.

A preferred embodiment of the present invention has been hereinbefore described with reference to a personal weather forecasting system. It will however be appreciated that the present invention is not limited in application to personal weather forecasting systems and may be applied to other services accessible via the Internet or similar networks. For example, in other embodiments of the present invention, there may be provided controlled access to a personal horoscope system in which the user requests a horoscope for a particular day in the future; a personal genealogy system for supplying ancestral information; and, an information system for supplying recipes based on ingredients input by the user.

To summarise then, what has now been described by way of example of the present invention is a system for controlling data access in a computer network comprising first means for establishing a first communication link between a client computer and a server computer. The client sends a request to the server for supply of a data item from the server to the client. The server selects the requested data item from a store of data items in response to the request from the client. The server associates each data item in the store with a service telephone number. The server also identifies a subscriber telephone number associated with the request. A second communication link is then established between the server and a telephone utility. The server instructs the telephone utility to register a telephone call from the subscriber telephone number to the service telephone number associated with the requested data item. The requested data item is supplied from the server to the client on receipt by the server of confirmation from the telephone utility that the telephone call is registered.

We claim:

1. A system for controlling data access in a computer network, the system comprising: first means for establishing a first communication link between a client computer and a server computer; means in the client for sending a request from the client to the server for supply of a data item from the server to the client; means in the server for selecting the requested data item from a store of data items in response to the request from the client; means in the server for associating each data item in the store with a service telephone number; means in the server for identifying a subscriber telephone number associated with the request; second means in the server for establishing a second communication link between the server and a telephone utility; means in the server for instructing the telephone utility to register a virtual telephone call from the subscriber telephone number to the service telephone number associated with the requested data item; and, means for supplying the requested data item from the server to the client on receipt by the server of confirmation from the telephone utility that the telephone call is registered.

2. A system as claimed in claim 1, wherein the first establishing means comprises a web browser for establishing the first communication link via the Internet.

3. A system as claimed in claim 1, wherein the store comprises a memory in the server system.

4. A system as claimed in claim 1, wherein the associating means comprises a look-up table stored in a memory of the server system.

5. A system as claimed in claim 1, wherein the client comprises means for identifying the subscriber telephone number to the server.

6. A system as claimed in claim 5, wherein the identifying means comprises a user input field for receiving a personal identification number from a user of the client.

7. A system as claimed in claim 1, wherein the service telephone number comprises a premium rate telephone number.

8. A system as claimed in claim 1, wherein the second establishing means generates the communication link between the server and the telephone utility via the Internet.

9. A system as claimed in claim 1, wherein the data item comprises a weather forecast.

10. A system as claimed in claim 9, wherein the client comprises means for specifying to the server the geographical location, day, and time desired for the weather forecast.

11. A method for controlling data access in a computer network, the method comprising: establishing a first communication link between a client computer and a server computer; sending a request from the client to the server for supply of a data item from the server to the client; selecting the requested data item from a store of data items in response to the request from the client; associating each data item in the store with a service telephone number; identifying a subscriber telephone number associated with the request; establishing a second communication link between the server and a telephone utility; instructing the telephone utility to register a virtual telephone call from the subscriber telephone number to the service telephone number associated with the requested data item; and, supplying the requested data item from the server to the client on receipt by the server of confirmation from the telephone utility that the telephone call is registered.

12. A personal weather forecasting system comprising: means for establishing a communication link between a client computer and a server computer; means in a client computer for sending a request from the client to the server for supply of a weather forecast from the server to the client; means in the server for selecting the requested weather forecast from a store of weather forecasts in response to the request from the client; and, means for supplying the requested weather forecast from the server to the client.

13. A system as claimed in claim 12, wherein the client comprises means for specifying to the server the geographical location, day, and time desired for the weather forecast.

14. A server computer system for controlling data access in a computer network, the system comprising: first means for establishing a first communication link to a client computer; means for receiving a request from the client for supply of a data item from the server to the client; means for selecting the requested data item from a store of data items in response to the request from the client; means for associating each data item in the store with a service telephone number; means for identifying a subscriber telephone number associated with the request; second means in said server for establishing a second communication link to a telephone utility; means for instructing the telephone utility to register a virtual telephone call from the subscriber telephone number to the service telephone number associated with the requested data item; and, means for supplying the requested data item to the client on receipt of confirmation from the telephone utility that the telephone call is registered.

15. A system as claimed in claim 14, having a memory comprising the store.

16. A system as claimed in claim 14, wherein the associating means comprises a look-up table stored in a memory of the server.

17. A system as claimed in claim 14, wherein the service telephone number comprises a premium rate telephone number.

18. A system as claimed in claim 14, wherein the second establishing means generates the communication link between the server and the telephone utility via the Internet.

* * * * *